(12) United States Patent
Ezrin et al.

(10) Patent No.: US 6,437,092 B1
(45) Date of Patent: Aug. 20, 2002

(54) CONJUGATES OF OPIOIDS AND ENDOGENOUS CARRIERS

(75) Inventors: Alan M. Ezrin, Moraga, CA (US); Dominique P. Bridon, Outremont; Darren L. Holmes, Montreal, both of (CA); Peter G. Milner, Los Altos Hills, CA (US)

(73) Assignee: Conjuchem, Inc., Montreal (CA)

( * ) Notice: Subject to any disclaimer, the term of this patent is extended or adjusted under 35 U.S.C. 154(b) by 0 days.

(21) Appl. No.: 09/445,986

(22) PCT Filed: Nov. 6, 1998

(86) PCT No.: PCT/US98/23704

§ 371 (c)(1), (2), (4) Date: Dec. 16, 1999

(87) PCT Pub. No.: WO99/24074

PCT Pub. Date: May 20, 1999

(51) Int. Cl.$^7$ .................................................. C07K 7/00
(52) U.S. Cl. .............................. 530/327; 514/2; 514/14; 530/345
(58) Field of Search ....................... 514/2, 14; 530/327, 530/345

(56) References Cited

U.S. PATENT DOCUMENTS

| | | | | |
|---|---|---|---|---|
| 4,361,553 A | 11/1982 | Loh et al. | .................... | 424/177 |
| 4,462,941 A | 7/1984 | Lee et al. | ................. | 260/112.5 |
| 5,017,689 A | 5/1991 | Hruby et al. | ................ | 530/327 |
| 5,376,662 A | 12/1994 | Ockert et al. | ................ | 514/282 |
| 5,482,930 A | 1/1996 | Wei et al. | ...................... | 514/13 |
| 5,612,034 A | 3/1997 | Pouletty et al. | .......... | 424/184.1 |
| 5,807,827 A | 9/1998 | Lee et al. | ..................... | 514/14 |
| 5,945,033 A | 8/1999 | Yen | ............................. | 252/314 |

FOREIGN PATENT DOCUMENTS

| | | |
|---|---|---|
| WO | WO 91/08220 | 6/1991 |
| WO | WO 93/25217 | 12/1993 |
| WO | WO 95/10302 | 4/1995 |
| WO | WO 96/06626 | 3/1996 |
| WO | WO 98/00171 | 1/1998 |
| WO | WO 99/24462 | 5/1999 |

OTHER PUBLICATIONS

Filho, Pharm Sci 2 199–201, 1996.*

Correa, Pharm Sci 3, 67–71, 1997.*

Dooley, et al. Six Highly Active MU–Selective Opioid Peptides Identified From Two Synthetic Combinatorial Libraries Peptide Research 8(3):124–137 (1995).

He, et al., Dynorphina—(2–17) Restores Spinal/Supraspinal Morphine Synergy in Morphine–Tolerant MICE1, Geraldine Brush Cance research Inst., Calif. Pac. Med. Ctr. Res. Ins., The J. of Pharm. & Experimental Therapeutics, 280:1210–1214 (1997).

Kieffer, et al. 32P–Labeled Opioid Peptides With High Affinity for the —Opioid Receptor Ecole Superieure de Biotechnologies, 1–8 (1993).

Krantz, A., Red Cell–Mediated Therapy: Opportunities and Challenges, Blood Cells, Molecules and Diseases 23(3):58–68 (1997).

Isom, G. E., Production and Characterization of Anti–Morphine Anti–Idiotypic Antibodies, Methodolgical Survey in Biochemistry and Analysis, 15:109–14 (1985).

Anand, et al., The Rat Brain Delta Opioid Receptor Studies with Anti–Idiotypic Antibodies to Anti–Leucine Enkephalin, Indiana Journal of Biochemistry & Biophysics, 30:117–122 (Apr. 93).

Cuello, et al., Characterization and Immunocytochemical Application of Monoclonal Antibodies Against Enkephalins, J. of Histochemistry and Cytochemistry, 32:(9)947–57 (1984).

Watkins, et al., Presence of B–Endorphin–Like Immunoreactivity in the Anterior Pituitary Gland of Rat and Man and Evidence for the Differential Localization with ACTH, Cell Tissue Res. 215 (3):577–89 (1981).

Borvendeg, et al., Radioimmunoassay of B–Endorphin: Immunoreactive Substances in the Brain and the Pituitary, Endorphins '78, Int'l Workshop Conf. Budapest, Hungary, Oct. 2–6, 1978, pp. 177–186 (1978).

Weissman, et al., Specific Antiserum to Leu–Enkephalin and its Use in a Radioimmunoassay, FEBS Letters, 70:(1)245–8 (1976).

* cited by examiner

Primary Examiner—Christopher S. F. Low
Assistant Examiner—David Lukton
(74) Attorney, Agent, or Firm—Morrison & Foerster LLP

(57) ABSTRACT

Conjugated are prepared from antinociceptive a agents, particularly opioids or opioid analoges, more particularly deltorphins, enkephalins or analogs thereof, by combining said antinociceptive agent with a material providing a functionally reactive group capable of reacting with a blood component (preferably cell or protein). Said conjugates permit extension of the therapeutic life of the antinociceptive agent. They may be administered to patients to alleviate pain, produce analgesic effects, or assist in cases of narcotics withdrawal, and may also be used as probes for receptor activity. The administration to the patient ma be made either in vivo or ex vivo and may be performed by either introducing the derivative including the reactive functional group into the patient's vascular system or preparing such a conjugate externally (or in vitro) and introducing that conjugate to the patient's vascular system.

16 Claims, No Drawings

SEQUENCE LISTING

<160> NUMBER OF SEQ ID NOS: 7

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence:Dynorphin
      analogue A(1-17)

<400> SEQUENCE: 1

Tyr Gly Gly Phe Leu Arg Arg Ile Arg Pro Lys Leu Lys Trp Asp Asn
  1               5                  10                  15

Gln

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence:Dynorphin
      analogue A(1-13)

<400> SEQUENCE: 2

Tyr Gly Gly Phe Leu Arg Arg Ile Arg Pro Lys Leu Lys
  1               5                  10

```
<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence:Dynorphin
      analogue A(2-13)

<400> SEQUENCE: 3

Gly Gly Phe Leu Arg Arg Ile Arg Pro Lys Leu Lys
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence:Dynorphin
      analogue A (1-13)
<220> FEATURE:
<223> OTHER INFORMATION: Xaa at position 1 is TFA-Tyr; Xaa at positions
      6, 7 and 9 are TFA-Arg; Xaa at position 11 is TFA-Lys and Xaa at
      position 13 is MPA-Lys. MPA is maleimidopropionic acid. TFA is
      trifluoroacetic acid.

<400> SEQUENCE: 4

Xaa Gly Gly Phe Leu Xaa Xaa Ile Xaa Pro Xaa Leu Xaa
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence:Dynorphin
      analogue A (1-13)
<220> FEATURE:
<223> OTHER INFORMATION: Xaa at position 1 is TFA-Tyr; Xaa at positions
      6, 7 and 9 are TFA-Arg; Xaa at position 11 is TFA-Lys and Xaa at
      position 13 is MPA-Lys. MPA is maleimidoproprionic acid. TFA is
      trifluoroacetic acid.

<400> SEQUENCE: 5

Xaa Gly Gly Phe Leu Xaa Xaa Ile Xaa Pro Xaa Leu Xaa
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence:Dynorphin
      analogue A(2-13)
<220> FEATURE:
<223> OTHER INFORMATION: Xaa at position 1 is TFA-Gly; Xaa at positions
      5, 6 and 8 are TFA-Arg; Xaa at position 10 is TFA-Lys; Xaa at
      position 12 is MPA-Lys. MPA is maleimidopropionic acid. TFA is
      trifluoroacetic acid.

<400> SEQUENCE: 6

Xaa Gly Phe Leu Xaa Xaa Ile Xaa Pro Xaa Leu Xaa
 1               5                  10

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence:Dynorphin
```

-continued

```
      analogue A (2-17)
<220> FEATURE:
<223> OTHER INFORMATION: Xaa at position 1 is MPA-Gly; Xaa at positions
      5, 6 and 8 are TFA-Arg; Xaa at position 10 is TFA-Lys; Xaa at
      position 12 is TFA-Lys. MPA is maleimidopropionic acid. TFA is
      trifluoroacetic acid.

<400> SEQUENCE: 7

Xaa Gly Phe Leu Xaa Xaa Ile Xaa Pro Xaa Leu Xaa Trp Asp Asn Gln
 1               5                  10                  15
```

CONJUGATES OF OPIOIDS AND ENDOGENOUS CARRIERS

FIELD OF THE INVENTION

This invention relates to conjugates of antinociceptive agents, notably opioids, and endogenous carriers, particularly to opioids and various blood components, particularly blood proteins.

BACKGROUND OF THE INVENTION

Antinociceptive agents comprise a large class of drugs that are used to alleviate pain. They include compounds such as steroids, analgesics, barbiturates and opioids.

The opioids comprise a large class of drugs, clinically used to relieve pain, and which include both plant-derived and synthetic alkaloids and peptides found indigenously in brains of mammals. The latter comprise three distinct families: beta-endorphin and other peptides derived from proopiomelanocortin, the enkephalins and the dynorphins. Opioids interact with neuronal cells and modulate physiological functions such as nociception. One of the physiological effects attributed to this class of compounds is analgesia.

While opioid drugs are used clinically to relieve pain their usefulness is limited by the tolerance and dependence that normally develops on chronic treatment. Opioid drugs such as morphine can be addictive and can have central mediated side effects such as respiratory and cardiac depressions and drowsiness. It would be desirable to develop therapeutic agents that could utilize the pain alleviating properties of the opioids without, or with lessened, central mediated side effects. It would also be desirable to be able to develop therapeutic agents which retain the positive properties of opioids and/or other antinociceptive agents for longer periods of time than is normally currently the case.

SUMMARY OF THE INVENTION

This invention relates to novel chemical reactive derivatives of antinociceptive agents, particularly opioids, which can react with available reactive functionalities on blood components to form covalent linkages, and in which the resulting covalently bound conjugates have antinociceptive activity.

As compared with the parent drugs the conjugated molecules have extended lifetimes in the bloodstream and are, therefore, capable of maintaining activity for extended periods of time as compared to the unconjugated parent drug, and of providing such activity with minimal or no centrally mediated side effects.

The invention also includes the conjugates of these drugs with blood components and methods for providing activity to a patient comprising administering to the bloodstream of a mammalian host the novel antinociceptive agent derivatives or the novel conjugates.

This invention relates to the use of the derivatives of this invention for the treatment of pain as well as to modify the immune response in patients.

This invention also relates to use of antibodies to locate and bind to such conjugates, for instance, to remove undesirable excesses of them from the host's blood stream.

BRIEF DESCRIPTION OF THE SEQUENCE LISTING

SEQ ID NO:1 is dynorphin A (1–17).
SEQ ID NO:2 is a dynorphin analogue, Dyn A (1–13).
SEQ ID NO:3 is a dynorphin analogue, Dyn A (2–13).
SEQ ID NO:4 is a derivative of Dyn A (1–13).
SEQ ID NO:5 is another derivative of Dyn A (1–13).
SEQ ID NO:6 is a derivative of Dyn A (2–13).
SEQ ID NO:7 is a derivative of Dyn A (2–17).

DETAILED DESCRIPTION OF THE INVENTION

To ensure a complete understanding of the invention, the following definitions are provided:

Antinociceptive agents: Antinociceptive agents are drugs that are used to alleviate pain. Antinociceptive agents include steroids, analgesics, barbiturates and opioids.

Opioids: Opioids are a large class of drugs, used clinically as painkillers, that include both plant-derived and synthetic alkaloids and peptides found endogenously in the mammalian brain. While the plant-derived alkaloids have been known and used for thousands of years, the endogenous opioid peptides were discovered only in the mid-1970s.

Opioids include endorphins, enkephalins, deltorphins, dynorphins, and analogs and derivatives of these. Of the opioids the dynorphins, and particularly dynorphin A and its derivatives and analogs, are preferred for use in this invention.

Dynorphins: Dynorphins are a class of endogenous opioids that exist in multiple forms in the central nervous system.

Dynorphins are derived from the precursor prodynorphin (proenkephalin B). Dynorphin, also known as Dynorphin A1–17, is a well-known opioid that has the sequence Tyr-Gly-Gly-Phe-Leu$^5$-Arg-Arg-Ile-Arg-Pro$^{10}$-Lys-Leu-Lys-Trp-Asp$^{15}$-Asn-Gln. SEQ ID NO:1. A number of derivatives and analogs of dynorphin are known including Dyn A1–13, SEQ ID NO: 2 Dyn A2–13, SEQ ID NO:3, Dyn A1–12, Dyn A2–12 and Dyn A2–17 as well as amide analogs such as those mentioned in U.S. Pat. No. 4,462,941 of Lee et al., N-terminus truncated dynorphin analogs such as those described in International Patent Application WO 96/06626 of Lee et al. and des-Tyr or des-Tyr-Gly analogs such as those disclosed in International Patent Application WO 93/25217 also of Lee et al.

Opioid Receptors: Opioid receptors are membrane bound receptors to which opioid molecules bind. Morphine binds to μopioid receptors. Enkephalins bind to δ opioid receptors. Dynorphin peptides bind to κ opioid receptors.

Receptor Agonists: Receptor agonists are chemical substances capable of activating a receptor to induce a full or partial pharmacological response.

Receptor Antagonists: Receptor Antagonists are chemical substances that are structurally related to a biologically active substance and which acts as an inhibitor.

Reactive Entities: Reactive entities are entities capable of forming a covalent bond. Such reactive agents are coupled or bonded to a therapeutic or diagnostic agent of interest. Reactive entities will generally be stable in an aqueous environment and will usually be a carboxyl, phosphoryl, or convenient acyl group, either as an ester or a mixed anhydride, or an imidate, thereby capable of forming a covalent bond with a group at the target site to form a derivative.

The reactive functionalities available on vascular proteins for covalent bond formation with the reactive group are primarily amino, carboxyl, hydroxyl and thiol groups.

Taking into account these definitions, this invention relates to compositions which are derivatives of antinociceptive agents, preferably of opioids, most preferably of dynorphins or a dynorphin derivative or analog, which can react with the available reactive functionalities on blood components via covalent linkages. The invention also relates to such derivatives, such combinations with blood components, and methods for their use. These methods include methods that extend the effect of therapeutic life of the drug in question as compared to administration of the parent drug per se to a patient, and methods for alleviating pain.

The derivative is of a type designated as a DAC (Drug Affinity Complex) which comprises the antinociceptive agent molecule and a linking group together with a chemically reactive group as described herein capable of reaction with a reactive functionality of a blood component, particularly of a blood protein. The blood protein may be blood derived, purified from blood or a recombinant blood protein. By reaction with the blood component or protein the derivative or DAC may be delivered via the blood to appropriate sites or receptors of the patient.

Derivatives of opioids and other antinociceptive agents which can conjugate with proteins and other blood components are prepared as is known in the art for other therapeutic drugs, e.g. as in U.S. Pat. No. 5,612,034, by the use of linking groups having chemically reactive groups which covalently bond to reactive functionalities on proteins, as described above. These reactive functionalities are primarily amino, carboxyl, hydroxyl and thiol groups. To form covalent bonds with the functional group on the protein, one may use as a chemically reactive group a variety of active groups. While a number of different reactive groups may be employed in these linking agents, the most convenient would be N-hydroxysuccinimidyl (NHS) and maleimido. The introduction of these groups may be accomplished, for example, by the use of N-hydroxysuccinimide (NHS), N-hydroxy-sulfosuccinimide (sulfo-NHS), maleimide-benzoyl-succinimide (MBS), gamma-maleimide-butyrylsuccinimide (GMBS), maleimidopropionic acid (MPA) or any agent affording an NHS ester or maleimido group. In the preferred embodiments of this invention, the functional group on this protein will be a thiol group and the chemically reactive group will be a maleimido-containing group.

Other linking agents that may be utilized are described in U.S. Pat. No. 5,612,034, which is hereby incorporated herein.

The antinociceptive agents which may be utilized in this invention are those which can be combined with such linking groups and chemically reactive groups, similarly to the opioids, so as to be capable of forming covalent bonds with functional groups on proteins.

To the extent that targeted bonding is employed, the choice of the long-lived blood component will be affected, at least in part, by the desired lifetime for the drug and the availability of the blood component for bonding to the opioid derivative. The various sites with which the chemically reactive group of the subject opioid derivatives may react include cells, particularly red blood cells (erythrocytes) and platelets, proteins, such as immunoglobulins, including IgG and IgM, serum albumin, ferritin, steroid binding proteins, transferrin, thyroxin binding protein, α-2-macroglobulin, and the like. Those proteins with which the derivatized opioids react, which are not long-lived, will generally be eliminated from the host within about three days. The proteins indicated above (including the proteins of the cells) will remain at least three days, and may remain five days or more (usually not exceeding 60 days, more usually not exceeding 30 days) particularly as to the half life, based on the concentration in the blood.

For the most part, reaction will be with mobile components in the blood, particularly blood proteins and cells, more particularly blood proteins and erythrocytes. By "mobile" is intended that the component does not have a fixed situs for any extended period of time, generally not exceeding 5, more usually one minute, although some of the blood component may be relatively stationary for extended periods of time. Initially, there will be a relatively heterogeneous population of functionalized proteins and cells. However, for the most part, the population within a few days will vary substantially from the initial population, depending upon the half-life of the functionalized proteins in the blood stream. Therefore, usually within about three days or more, IgG will become the predominant functionalized protein in the blood stream.

Usually, by day 5 post-administration, IgG, serum albumin and erythrocytes will be at least about 60 mole %, usually at least about 75 mole %, of the conjugated components in blood, with IgG, IgM (to a substantially lesser extent) and serum albumin being at least about 50 mole %, usually at least about 75 mole %, more usually at least about 80 mole %, of the non-cellular conjugated components.

Preferably, the antinociceptive agent or opioid derivative is conjugated to albumin. Such conjugation is preferably established by covalent bonding of a maleimide (e.g., prepared from GMBS, MPA or another maleimido group) to a thiol group on the albumin. As there is only a single thiol group on albumin, conjugates will tend to comprise approximately a 1:1 ratio of opioid derivatives to albumin. This is in opposition to typical conjugation techniques that result in multiple copies of the therapeutic drug in question being covalently bound to a single albumin molecule.

If desired, the subject conjugates may also be prepared ex vivo by combining blood with derivatized opioids or other agents of the present invention, allowing covalent bonding of the derivatized drugs to reactive functionalities on blood components and then returning or administering the conjugated blood to the host. Moreover, the above may also be accomplished by first purifying an individual blood component or limited number of components, such as red blood cells, immunoglobulins, serum albumin, or the like, and combining the component or components ex vivo with the chemically reactive derivatives. The functionalized blood or blood component may then be returned to the host to provide in vivo the subject therapeutically effective conjugates. The blood also may be treated to prevent coagulation during handling ex vivo.

Some blood components such as hemoglobin are known to possess comparatively high permeability across the blood-nerve and blood-brain barriers. One focus of a preferred embodiment of this invention utilizes the ability of albumin to enter the interstitial space and gain access to peripheral neurons so as to deliver modified opioid molecules to pain receptors to influence pain transmission via the stimulation of peripheral opioid receptors. Clinical data has suggested that peripheral opioid receptors can be a potential target for relevant antinociceptive activity of morphine-like drugs and be effective in limiting pain without the need for penetration into the central nervous system (Stein et al., 1991). The major limitations of existing opioid-like drugs include central mediated side effects (respiratory and cardiac depressions), addictive potential and down regulation or loss of efficacy. In contrast drugs bound to plasma proteins such as albumin would retain activity and be devoid of the central mediated side effects such as cardiac and respiratory depression and addiction. Preferably the conjugates of this invention are constructed so as to selectively react and covalently bond with thiol groups on proteins, most preferably with proteins which do not cross the blood-brain or blood-nerve barriers. Such conjugates can deliver the antinociceptive effect of the drug without effect on the brain or on the central nervous system. However, should it be desirable to produce conjugates that can cross these barriers, then the antinociceptive agent is derivatized with a more generally reactive group such as a succinimide. Such derivatives can react with various blood proteins and other components non-selectively, so that the possible conjugates include those that can cross the barrier. Therefore, in a preferred embodiment of this invention, to aid in minimizing centrally mediated side effects, in addition to constructing the derivatives so as to conjugate primarily with albumins, the ratio of antinociceptive derivatives to blood is controlled so as to take advantage of this comparatively large amount of albumin (the preferred blood component for forming conjugates) in the blood. Preferably, the amount of antinociceptive derivatives added to blood in vivo or ex vivo is from about 0.01 $\mu$mol/kg to about 100 $\mu$mol/kg, most preferably from about 1 $\mu$mol/kg to about 30 $\mu$mol/kg.

Thus, the derivative of the antinociceptive agent (or opioid) may be designed either for random (nonselective) or targeted (selective) bonding, with blood components in general, or with selected components (such as albumin). Targeted or selective bonding may be accomplished, as described above, by incorporating into the derivative a reactive group that will selectively bond to a desired blood component. Alternatively one may prepare a combinatorial library and screen for members of that library which provide the desired blood component association spectrum.

A conjugate of an opioid of this general type was prepared in Kieffer, et al., *Analytical Biochemistry vol.* 215 p. 1 (1993) from a peptide prepared by the authors (designated Peptide B in the reference), with bovine albumin (BSA) via a maleimide linker (MBS). Peptide B has the sequence YdAGFLTPRRASLGC, in which dA stands for d-alanine. The conjugate was determined to have better binding potency for the $\delta$-opioid receptor than Peptide B itself. However, no mention is made of any therapeutic effect of this conjugate.

The desired conjugates of opioids or other antinociceptive drugs to blood components may be prepared in vivo by administration of the opioid or other derivative to the patient, which may be a human or other animal. The administration may be done in the form of a bolus or introduced slowly over time by infusion using metered flow or the like. Alternatively, blood may be removed from the host, treated ex vivo and returned to the host. Another application requires ex vivo conjugation of the opioid or other derivative to a commercial source of plasma protein (e.g.-albumin) followed by infusion to the host.

For in vivo or ex vivo conjugate formation, the drug derivatives will be administered in a physiologically acceptable medium, e.g. deionized water, phosphate buffered saline (PBS), saline, aqueous ethanol or other alcohol, plasma, proteinaceous solutions, mannitol, aqueous glucose, alcohol, vegetable oil, or the like. If necessary a small amount of a physiologically acceptable solvent or co-solvent such as DMSO may be included. Other additives which may be included include buffers, where the media are generally buffered at a pH in the range of about 5 to 10, where the buffer will generally range in concentration from about 50 to 250 mM, salt, where the concentration of salt will generally range from about 5 to 500 mM, physiologically acceptable stabilizers, and the like. The compositions may be lyophilized for convenient storage and transport.

The subject drug derivatives will for the most part be administered parenterally, such as intravascularly, (IV), intraocular (IO), intraarterially (IA), intramuscularly (IM), subcutaneously (SC), or the like. Administration may in appropriate situations be by transfusion. In some instances, where reaction of the active functional group is relatively slow, administration may be oral, nasal, rectal, transdermal or aerosol, where the nature of the conjugate allows for transfer to the vascular system. Usually a single injection will be employed although more than one injection may be used, if desired. The drug derivatives may be administered by any convenient means, including syringe, trocar, catheter, or the like. The particular manner of administration will vary depending upon the amount to be administered, whether a single bolus or continuous administration, or the like. Preferably, the administration will be intravascularly, where the site of introduction is not critical to this invention, preferably at a site where there is rapid blood flow, e.g., intravenously, peripheral or central vein. Other routes may find use where the administration is coupled with slow release techniques or a protective matrix. The intent is that the antinociceptive agent, particularly the opioid, dynorphin analog, or derivative be effectively distributed in the blood, so as to be able to react with the blood components. The concentration of the conjugate will vary widely, generally ranging from about 1 pg/ml to 50 mg/ml. The total administered intravascularly will generally be in the range of about 0.1 mg/ml to about 10 mg/ml, more usually about 1 mg/ml to about 5 mg/ml.

By bonding to long-lived components of the blood, such as immunoglobulin, serum albumin, red blood cells and platelets, a number of advantages ensue. The activity of the drug is extended for days to weeks. Only one administration need be given during this period of time. Greater specificity can be achieved, since the active compound will be primarily bound to large molecules, where it is less likely to be taken up intracellularly to interfere with other physiological processes.

The blood of the mammalian host may be monitored for the presence of the drug one or more times. By taking a portion or sample of the blood of the host, one may determine whether the drug has become bound to the long-lived blood components in sufficient amount to be therapeutically active and, thereafter, the level of that compound in the blood. If desired, one may also determine to which of the blood components the drug or its derivative molecule is bound.

Thus, this invention relates to such conjugates of antinociceptive agents, particularly opioids, opioid analogs and their derivatives with blood components, particularly blood proteins such as albumin, as well as methods of administrating them to human and other animal patients.

Another aspect of this invention relates to methods for determining the concentration of the drug, or its derivatives and conjugates in biological samples (such as blood) using antibodies specific to the antinociceptive agent or its derivatives and conjugates, and to the use of such antibodies as a treatment for toxicity potentially associated with such drugs or conjugates. This is advantageous because the increased stability and life of the drugs in vivo in the patient might lead to novel problems during treatment, including increased possibility for toxicity. The use of anti-therapeutic agent antibodies, either monoclonal or polyclonal, having specificity for a particular antinociceptive agent or derivative thereof, can assist in mediating any such problem. The antibody may be generated or derived from a host immunized with the particular drug or derivative thereof, or with an immunogenic fragment of the agent, or a synthesized immunogen corresponding to an antigenic determinant of the agent. Preferred antibodies will have high specificity and affinity for native, derivatized and conjugated forms of the antinociceptive agent. Such antibodies can also be labeled with enzymes, fluorochromes, or radio labels.

The anti-therapeutic agent antibodies may be used to treat toxicity induced by administration of the antinociceptive agent or derivative thereof, and may be used ex vivo or in vivo. Ex vivo methods would include immuno-dialysis treatment for toxicity employing anti-therapeutic agent antibodies fixed to solid supports. In vivo methods include administration of anti-therapeutic agent antibodies in amounts effective to induce clearance of antibody-agent complexes.

The antibodies may be used to remove the antinociceptive agent, and conjugates thereof, from a patient's blood ex vivo by contacting the blood with the antibodies under sterile conditions. For example, the antibodies can be fixed or otherwise immobilized on a column matrix and the patient's blood can be removed from the patient and passed over the matrix. The antinociceptive agent or conjugates will bind to the antibodies and the blood containing a low concentration of the antinociceptive agent or conjugate, then may be returned to the patient's circulatory system. Adjusting the pressure and flow rate can control the amount of antinociceptive agent removed. Preferential removal of the antinociceptive agent and conjugates from the serum component of a patient's blood can be effected, for example, by the use of a semipermeable membrane, or by otherwise first separating the serum component from the cellular component by ways known in the art prior to passing the serum component over a matrix containing the anti-therapeutic antibodies. Alternatively the preferential removal of conjugated blood cells, including red blood cells, can be effected by collecting and concentrating the blood cells in the patient's blood and contacting those cells with fixed anti-therapeutic antibodies to the exclusion of the serum component of the patient's blood.

The anti-therapeutic antibodies can be administered in vivo, parenterally, to a patient that has received the antinociceptive agents or conjugates for treatment. The antibodies will bind the compounds and conjugates. Once bound the drug's activity will be hindered if not completely blocked thereby reducing the biologically effective concentration of antinociceptive agents in the patient's bloodstream and minimizing harmful side effects. In addition, the bound antibody-drug complex will facilitate clearance of the antinociceptive agents and conjugates from the patient's blood stream.

The derivatives and conjugates of the antinociceptive agents may be used in several different ways and to achieve several different ends. As mentioned above, these materials may be used in place of typical antinociceptive agents for alleviating pain. As compared with drugs currently available, the materials of this invention can alleviate pain without central mediated side effects or potential of addiction or loss of efficacy, and are available for alleviating pain for a substantially longer time than conventionally administered drugs. Opioid derivatives and conjugates of this invention also may be utilized (in accordance with U.S. Pat. No. 5,482,930) as anti-inflammatory and/or anti-irritation agents or in general to inhibit vascular leakage from tissues. In addition, as is known in the art, these materials may be used to treat hosts which are or have become tolerant to morphine (or to treat patients undergoing methadone treatment programs), as well as treatment of narcotics withdrawal in general. The conjugates and materials of this invention in addition, when labeled, may be utilized for experimental purposes such as probes to investigate biological functions of various receptors.

The invention is further illustrated by the following examples.

Experimental Section

General

Syntheses of all dynorphin A analogs were performed using manual solid-phase synthesis and an ABI 433A Peptide Synthesizer using 0.55 mmol/g of Fmoc protected Rink Amide MBHA resin (NovaBiochem), 4 eq. of Fmoc protected amino acids, 4 eq of a 0.45 M 0-benzotriazol-1-yl-N,N, N', N'-tetramethyl-uronium hexafluorophosphate (HBTU) and 1-hydroxybenzotriazole (HOBt) in N,N-dimethylformamide solution as activation with 4 eq. of 2 M N,N,-diisopropylethylamine (DIEA) in 1-methyl-2-pyrrolidinone (NMP), and piperidine deprotection of Fmoc groups. Side chain derivatization of the carboxy-terminal lysine residue was accomplished using Fmoc-Lys(Mtt)-OH (NovaBiochem) and deprotection of the methyltrityl (Mtt) group was accomplished with 5% trifluoroacetic acid (TFA)/ 5% triisopropylsilane (TIS) in dichloromethane (DCM). Derivatives with free amino-terminal amino acid residues were synthesized using either Boc-Tyr(tBu)-OH (NovaBiochem) or Boc-Gly-OH (Advanced Chem T ech). Resin cleavage and product isolation were all perform ed u sing 95% TFA/2.5% TIS/2.5% $H_2O$, followed by dry-ice cold $Et_2O$ precipitation. All dynorphin A analogs were purified by preparative reversed phased HPLC using a Varian (Rainin) preparative binary HPLC system: gradient elution of 5–60% B (0.045% TFA in H2O (A) and 0.045% TFA in $CH_3CN$ (B)) at 9.5 mL/min using a Dynamax $C_{18}$, 60Å, 8 µm, 21 mm×25 cm column equipped with a Dynamax $C_{18}$, 60Å, 8 µm guard module and an UV detector (Varian Dynamax UVD II) at 214 and 254 nm. Analytical HPLC were performed using a Varian (Rainin) binary HPLC system: gradient elution of 5–60% B (0.045% TFA in $H_2O$ (A) and 0.045% TFA in $CH_3CN$ (B)) at 0.5 mL/min using a Dynamax $C_{18}$, 60Å, 8 µm, 4.6 mm×25 cm column equipped with a Dynamax $C_{18}$, 60Å, 8µm guard module and an UV detector (Varian Dynamax UVD II) at 214 and 254 nm. Mass spectrometry was performed on a PE Sciex API III electro-spray Biomolecular Mass Analyzer.

Note that TFA would not be acceptable for inclusion in a product intended for use in humans, so that a human-compatible protective agent such as HCl would be used.

EXAMPLE 1
Synthesis of Dyn A 1–13(MPA)-$NH_2$

Using automated peptide synthesis, the following protected amino acids were sequentially added to Ring Amide MBHA resin: Fmoc-Lys(Mtt)-OH, Fmoc-Leu-OH, Fmoc-Lys(Boc)-OH, Fmoc-Pro-OH, Fmoc-Arg(Pbf)-OH, Fmoc-Ile-OH, Fmoc-Arg(Pbf)-OH, Fmoc-Arg(Pbf)-OH, Fmoc-Leu-OH, Fmoc-Phe-OH, Fmoc-Gly-OH, Fmoc-Gly-OH, and Boc-Tyr(Boc)-OH. Manual synthesis was employed for the remaining steps: selective removal of the Mtt group and coupling of maleimidopropionic acid (MPA) using HBTU/HOBt/DIEA activation in DMF. The target dynorphin analog was removed from the resin; the product was isolated by precipitation and purified by preparative HPLC to afford the desired product as a white solid upon lyophilization in a 42% yield. Anal. HPLC indicated product to be >95% pure with $R_f$=33.00 min. ESI-MS m/z for $C_{82}H_{133}N_{26}O_{17}$ ($MH^+$), calcd 1754.0, found 1754.4, $MH^{3+}$ 585.8.

The structure of this product is

EXAMPLE 2
Synthesis of Dyn A 2–13(MPA)-$NH_2$

Using automated peptide synthesis, the following protected amino acids were sequentially added to Ring Amide MBHA resin: Fmoc-Lys(Mtt)-OH, Fmoc-Leu-OH, Fmoc-Lys(Boc)-OH, Fmoc-Pro-OH, Fmoc-Arg(Pbf)-OH, Fmoc-Ile-OH, Fmoc-Arg(Pbf)-OH, Fmoc-Arg(Pbf)-OH, Fmoc-Leu-OH, Fmoc-Phe-OH, Fmoc-Gly-OH, and Boc-Gly-OH. Manual synthesis was employed for the remaining steps: selective removal of the Mtt group and coupling of MPA using HBTU/HOBt/DIEA activation in DMF. The target dynorphin analog was removed from the resin; the product was isolated by precipitation and purified by preparative HPLC to afford the desired product as a white solid upon lyophilization in a 35% yield. Anal. HPLC indicated product to be >95% pure with $R_f$=30.42 min. ESI-MS m/z for $C_{73}H_{123}N_{25}O_{15}$ ($MH^+$), calcd 1590.0, found $MH^{3+}$ 531.3.

EXAMPLE 3
Synthesis of Dyn A 1–13($AEA_3$-MPA)-$NH_2$

Using automated peptide synthesis, the following protected amino acids were sequentially added to Ring Amide MBHA resin: Fmoc-Lys(Mtt)-OH, Fmoc-Leu-OH, Fmoc-Lys(Boc)-OH, Fmoc-Pro-OH, Fmoc-Arg(Pbf)-OH, Fmoc-Ile-OH, Fmoc-Arg(Pbf)-OH, Fmoc-Arg(Pbf)-OH, Fmoc-Leu-OH, Fmoc-Phe-OH, Fmoc-Gly-OH, Fmoc-Gly-OH, and Boc-Tyr(Boc)-OH. Manual synthesis was employed for the remaining steps: selective removal of the Mtt group, the coupling of three-Fmoc-AEA-OH groups (AEA= aminoethoxyacetic acid) with Fmoc removal in-between each coupling, and MPA acid using HBTU/HOBt/DIEA activation in DMF. The target dynorphin analog was removed from the resin; the product was isolated by precipitation and purified by preparative HPLC to afford the desired product as a white solid upon lyophilization in a 29% yield. Anal. HPLC indicated product to be >95% pure with $R_f$=33.06 min. ESI-MS m/z for $C_{94}H_{154}N_{29}O_{23}$ ($MH^+$), calcd 2057.2, found $MH^{4+}$515.4, $MH^{3+}$686.9, $MH^{2+}$1029.7.

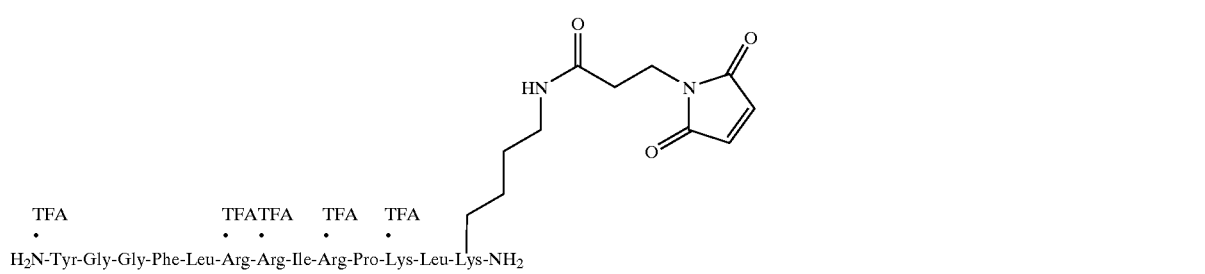

The structure of this product is

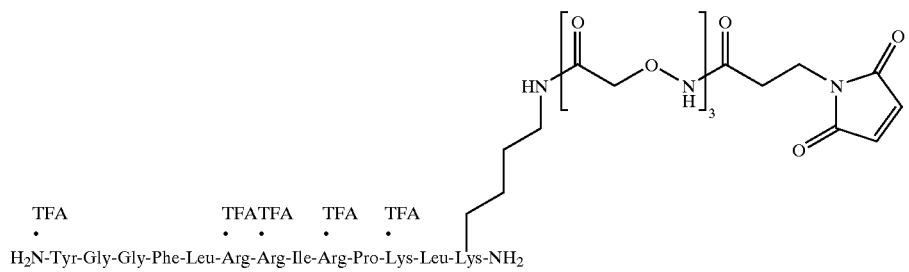

TFA          TFATFA   TFA   TFA
•               •    •     •     •
H$_2$N-Tyr-Gly-Gly-Phe-Leu-Arg-Arg-Ile-Arg-Pro-Lys-Leu-Lys-NH$_2$

EXAMPLE 4
Synthesis of Dyn A 2–13(AEA$_3$-MPA)-NH$_2$

Using automated peptide synthesis, the following protected amino acids were sequentially added to Ring Amide MBHA resin: Fmoc-Lys(Mtt)-OH, Fmoc-Leu-OH, Fmoc-Lys(Boc)-OH, Fmoc-Pro-OH, Fmoc-Arg(Pbf)-OH, Fmoc-Ile-OH, Fmoc-Arg(Pbf)-OH, Fmoc-Arg(Pbf)-OH, Fmoc-Leu-OH, Fmoc-Phe-OH, Fmoc-Gly-OH, and Fmoc-Gly-OH. Manual synthesis was employed for the remaining steps: selective removal of the Mtt group, the coupling of three-Fmoc-AEA-OH groups, with Fmoc removal in-between each coupling, and MPA using HBTU/HOBt/DIEA activation in DMF. The target dynorphin analog was removed from the resin; the product was isolated by precipitation and purified by preparative HPLC to afford the desired product as a white solid upon lyophilization in a 29% yield. Anal. HPLC indicated product to be >95% pure with R$_t$=31.88 min. ESI-MS m/z for C$_{85}$H$_{145}$N$_{25}$O$_{21}$ (MH$^+$), calcd 1894.3, found MH$^{4+}$ 474.6, MH$^{3+}$ 632.4, MH$^{2+}$ 948.10.

The structure of this product is

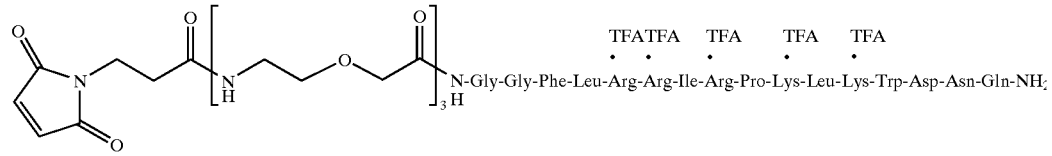

TFATFA   TFA     TFA     TFA
•   •     •       •       •
N-Gly-Gly-Phe-Leu-Arg-Arg-Ile-Arg-Pro-Lys-Leu-Lys-Trp-Asp-Asn-Gln-NH$_2$ (Trt)-OH, Fmoc-Asp(OtBu)-OH, Fmoc-Trp(Boc)-OH, Fmoc-Lys(Boc)-OH, Fmoc-Leu-OH, Fmoc-Lys(Boc)-OH, Fmoc-Pro-OH, Fmoc-Arg(Pbf)-OH, Fmoc-Ile-OH, Arg(Pbf)-OH, Fmoc-Arg(Pbf)-OH, Fmoc-Leu-OH, Fmoc-Phe-OH, Fmoc-Gly-OH, Fmoc-Gly-OH, Fmoc-AEA-OH, Fmoc-AEA-OH, Fmoc-AEA-OH, and MPA. The target dynorphin analog was then removed from the resin; the product was isolated by precipitation and purified by preparative HPLC to afford the desired product as a pale yellow solid upon lyophilization in a 32% yield. Anal. HPLC indicated product to be >95% pure with R$_t$=33.44 min. ESI-MS m/z for C$_{109}$H$_{172}$N$_{35}$O$_{29}$ (MH$^+$), calcd 2436.8, found MH$^{3+}$ 813.6.

The structure of this product is

EXAMPLE 6
Preparation of Dynorphin-Human Serum Albumin Conjugates (Ex Vivo Preparation In 10 mL reaction vials were placed 4.95 mL of 20% HSA.

To that was added 50.0 μL of a 10 mM solution of the dynorphin derivative prepared in Example 1, 3, 4 or 5 dissolved in water. These mixtures were allowed to stand at room temperature for 3 hours, then analyzed by reverse-

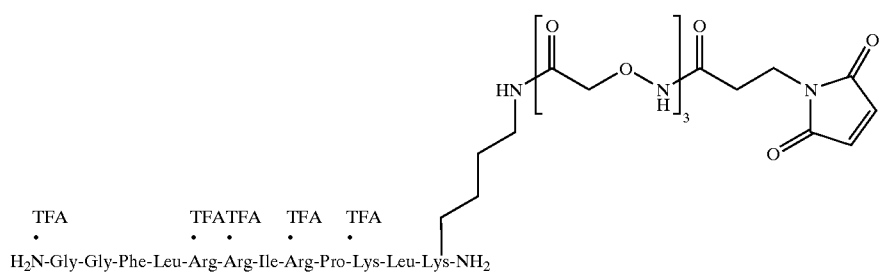

TFA          TFATFA   TFA   TFA
•               •    •     •     •
H$_2$N-Gly-Gly-Phe-Leu-Arg-Arg-Ile-Arg-Pro-Lys-Leu-Lys-NH$_2$

EXAMPLE 5
Synthesis of MPA-AEA$_3$-Dyn A 2–17-NH$_2$

Using automated peptide synthesis, the following protected amino acids and maleimide were sequentially added to Ring Amide MBHA resin: Fmoc-Gln(Trt)-OH, Fmoc-Asn phase HPLC, which showed the absence of the starting dynorphin derivative.

EXAMPLE 7
Non-selective Binding Assay

Non-selective binding of the conjugates produced above was assayed using Naloxone as follows.

Binding Reaction

1. Each tube receives the following components:
   - 25 µL drug or vehicle
   - 25 µL $^3$H-Naloxone
   - 200 µL tissue suspension (rat brain homogenate)
2. Initiate the binding reaction with the addition of tissue, and incubate for 90 minutes at 25° C.
3. Terminate the binding reaction by rapid vacuum filtration of the assay contents onto untreated GF/B filters.
4. Rinse the tubes once with ice-cold 50 mM TRIS•EHCl (pH 7.4, at 25° C.), then rinse the filters with approximately 7 mL/tube of the same ice-cold wash buffer.
5. Radioactivity trapped on the filters is assessed using liquid scintillation spectrophotometry.

Materials and Reagents

1. [$^3$H]-Naloxone is diluted in 50 mM Tris-HCl (pH 7.4 at 25° C.) to a concentration of 10 nM, such that the final radioligand concentration in this assay is 1.0 nM.
2. Non-specific binding is defined as that remaining in the presence of 1 µM Naloxone.
3. The reference compound is Naloxone at final concentrations of: $3\times10^{-11}$, $1\times10^{-10}$, $3\times10^{-10}$, $1\times10^{-9}$, $3\times10^{-9}$, $1\times10^{-8}$, $3\times10^{-8}$, $1\times10^{-7}$, and $3\times10^{-7}$ M.
4. The positive control is Naloxone run at final concentrations of $3\times10^{-9}$, $3\times10^{-8}$ and $3\times10^{-7}$ M.
5. The $K_d$ of the mu opiate receptor for [$^3$H]-Naloxone is 2.0 nM.

The assay was conducted using HSA and the initial dynorphins (A 1–13, A 2–13 and A 2–17) as reference standards for Naloxone inhibition. Tested for inhibition were the conjugates made in Example 6 above. Results are tabulated in Table 1 and demonstrate that three of the four conjugates showed Naloxone inhibition comparable to the parent dynorphin.

| ENTRY | COMPOUND | % INHIBITION AT | | |
|---|---|---|---|---|
| | | 0.1 nM | 10 nM | 1000 nM |
| 1 | HAS | −0.6 | 8.04 | −8.05 |
| 2 | Dynorphin A 1-13-NH$_2$ | 2.76 | 9.89 | 91.78 |
| 3 | Dynorphin A 2-13-NH$_2$ | 1.66 | −0.19 | 44.07 |
| 4 | Dynorphin A 2-17-NH$_2$ | −3.21 | 4.87 | 12.69 |
| 5 | CCl-E (20% HSA•Dyn A 1-13(MPA)_NH$_2$ | −0.76 | 8.27 | 93.66 |
| 6 | CCl-F (20% HSA•Dyn A 2-13(AEA$_3$-MPA)-NH$_2$ | 9.11 | 1.40 | 45.15 |
| 7 | CCl-G (20% HSA•Dyn A 1-13(AEA$_3$-MPA)-NH$_2$ | 3.72 | 5.37 | 86.35 |
| 8 | CCl-H (20% HAS•MPA-AEA$_3$-Dyn A 2-17-NH$_2$ | 3.23 | 1.28 | −4.06 |

The only conjugate which did not show inhibition was CCl-H. This conjugate (and its predecessor derivative prepared in Example 5) differs from the others in that the conjugation was produced by derization of the amino terminus of the dynorphin rather than of the carboxyl terminus.

In addition, CCl-H was formed from a des-Tyr dynorphin derivative, Dyn A 2–17.

The fact that conjugates CCl-E and -G function ed as well as Dyn A 1–13-NH$_2$ in this assay is surprising. Equally effective was CCl-F, inhibiting similarly to Dyn A 2-1 3-NH$_2$. These data suggest that the dynorphin conjugates are equipotent to the native dynorphin pepdtides.

EXAMPLE 8
In Vivo Experiments

The following assay was conducted to show antinociceptive activity of dynorphin-albumin conjugates prepared in vivo and ex vivo with 20% HSA in mice.

The materials tested were:

Group A: Morphine (10 µmol/kg or 3 mg/kg), 20% HSA (1 i.e. 250 µL), 0.9% saline.

Group B: Dynorphin A 1–13-NH$_2$ salt (10 µmol/kg or 20 mg/kg), CCl-1017 (10 µmol/kg or 696 mg/kg) as ex-vivo conjugate, and CCl-1008 (30 µmol/kg or 70 mg/kg) as in-vivo conjugate.

Group C: Dynorphin A 2–13-NH$_2$ salt (10 µmol/kg or 18 mg/kg), CCl-1018 (10 µmol/kg or 697 mg/kg) as ex-vivo conjugate, and CCl-1010 (30 µmol/kg or 77 mg/kg) as in-vivo conjugate.

Group D: CCl-1019 (10 µmol/kg or 699 mg/kg) as ex-vivo conjugate, and CCl-1009 (30 µmol/kg or 79 mg/kg) as in-vivo conjugate.

Group E: Dynorphin A 2–17-NH$_2$ salt (10 µmol/kg or 25 mg/kg), CCl-1020 (10 µmol/kg or 70 mg/kg) as ex-vivo conjugate, and CCl-1011 (30 µmol/kg or 90 mg/kg) as in-vivo conjugate.

Each treatment group consisted of four time points (5 min, 1 hour, 3 hours, and 24 hours) with three male mice/dose/time point.

Experimental procedure:

Writhing assay (Hooke, L. P.; Lee, N. M. *J. Pharmacol. Exp. Ther.* 1995, 273, 802–807 and Hayashi, G.; Takemori, A. E. *Eur. J. Phannacol.* 1971, 16, 63–66)

Approximately 1 h before the writhing assay, the mice are placed individually in transparent observation chambers for an adaptation period.

The number of abdominal stretches (writhes) are counted for a period of 6 min: this will be the baseline response for the assay.

Test substance (250, µL volumes) is injected as bolus via the tail vein. At the given time periods (5 min, 1 hour, 3 hours, 24 hours) after injection of test material, the mice are injected i.p. with 2 mg/kg acetic acid (HOAc)

Five minutes after HOAc administration, mice are placed into transparent cylinders and the number of abdominal stretches (writhes) are counted for a period of 6 min. The average of stretches are compared to that of control (0.9% saline) group. Antinociception activity is expressed as % inhibition of the average writhes in the control group (typically 18–25).

The data is shown below in Table 2.

TABLE 2

| Compound | Dose (μmol/kg) | N | 5 min. post i.v. injection of TA | | 1 h post i.v. injection of TA | | 3 h post i.v. injection of TA | | 24 h post i.v. injection of TA | |
|---|---|---|---|---|---|---|---|---|---|---|
| | | | Average writhes | % Inh. | Average writhes | % Inh. | Average writhes | % Inh. | Average writhes | % Inh. |
| Saline | 10 mL/kg | 3 | 19 | 0 | 16 | 0 | 15 | 0 | 16 | 0 |
| Morphine | 3 mg/kg | 3 | 0 | 100 | 0 | 100 | 5 | 67 | 7 | 56 |
| 20% HSA | 30 | 3 | 15 | 21 | 13 | 19 | 13 | 13 | 13 | 19 |
| Dyn A 1-13-NH$_2$ | 3[a,b] | 3 | 8 | 58 | ND | ND | ND | ND | 17 | 0 |
| Dyn A 2-13-NH$_2$ | 3[a,c] | 3 | 5 | 74 | ND | ND | 17[c] | 0[c] | 17 | 0 |
| Dyn A 2-17-NH$_2$ | 3[a,c] | 3 | 5 | 74 | ND | ND | 15[c] | 0[c] | 15 | 6 |
| CCl-A | 30 | 3 | 9 | 53 | 3[d] | 81[d] | 8[d] | 47[d] | 12 | 25 |
| CCl-B | 30 | 3 | 0 | 100 | 9[d] | 44[d] | 4[d] | 73[d] | 16 | 0 |
| CCl-C | 30 | 3 | 14 | 26 | 17 | 0 | 15 | 0 | 17 | 0 |
| CCl-D | 30 | 3 | 3 | 84 | 13 | 19 | 16 | 0 | 13 | 19 |
| CCl-E | 10 | 3 | 14 | 26 | 0 | 100 | 19 | 0 | 12 | 25 |
| CCl-F | 10 | 3 | 15 | 21 | 11 | 31 | 17 | 0 | 13 | 19 |
| CCl-G | 10 | 3 | 12 | 37 | 1 | 94 | 5 | 67 | 11 | 31 |
| CCl-H | 10 | 3 | 14 | 26 | 16 | 0 | 14 | 7 | 16 | 0 |

[a]At 30 μmol/kg three out of three animals died within 5 min. after i.v. injection of TA.
[b]At 10 μmol/kg three out of three animals died within 5 min. after i.v. injection of TA.
[c]At 10 μmol/kg one out of three animals died within 5 min. after i.v. injection of TA.
[d]At 30 μmol/kg one out of three animals died within 5 min. after i.v. injection of TA.

The data in this table show the conjugates CCl-E and G, prepared ex vivo in Example 6 were potent, after a delayed onset, and show a sustained duration of action. Interestingly, the destyrosine derivatives, CCl-F and CCl-H showed little initial effect and no sustained duration. Furthermore, in vivo administration showed moderate initial activity and over time duration was sustained and the activity profile resembled that of morphine, thus demonstrating the ability to form the conjugate to the native albumin in vivo

What is claimed is:

1. A compound of the formula:

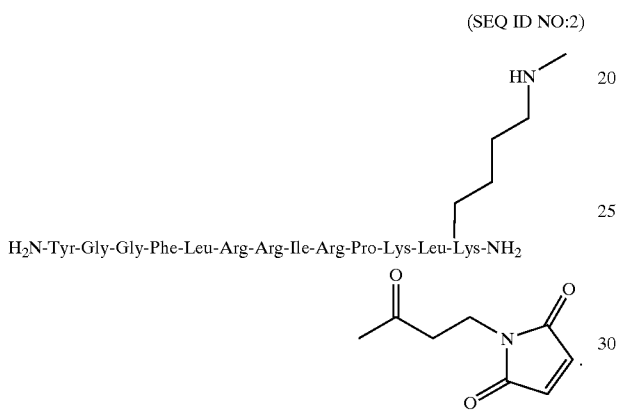

(SEQ ID NO:2)

H₂N-Tyr-Gly-Gly-Phe-Leu-Arg-Arg-Ile-Arg-Pro-Lys-Leu-Lys-NH₂

2. A composition comprising the compound of claim 1 and physiologically acceptable carrier.

3. A method of treating pain in a patient suffering therefrom comprising administering to the patient a compound according to claim 1 for a time and under conditions effective to induce analgesia.

4. A method according to claim 3 wherein the compound is administered as a bolus.

5. A method according to claim 3 wherein the compound is administered continuously.

6. A method of treating pain in a patient suffering therefrom comprising administering a composition as claimed in claim 2 for a time and under conditions effective to induce analgesia.

7. A method according to claim 6 wherein the composition is administered as a bolus.

8. A method according to claim 6 wherein the composition is administered continuously.

9. A method of treating pain in a patient suffering therefrom comprising:

a) reacting the compound of claim 1 with a blood protein bearing a thiol group for a time and under conditions effective to form a covalent bond between the thiol group on the blood protein and the maleimide group in the compound, thereby forming a conjugate; and b) adding a physiological carrier to said conjugate to form a composition; and c) administering the composition to the patient for a time and under conditions effective to induce analgesia.

10. A method according to claim 9 wherein the blood protein is serum albumin.

11. A method according to claim 9 wherein the composition is administered as a bolus.

12. A method according to claim 9 wherein the composition is administered continuously.

13. A method of treating pain in a patient suffering therefrom comprising:

a) reacting the compound of claim 1 with a blood protein bearing a thiol group for a time and under conditions effective to form a covalent bond between the thiol group on the blood protein and the maleimide group in the compound, thereby forming a conjugate; and b) administering the conjugate to the patient for a time and under conditions effective to induce analgesia.

14. The method according to claim 13 wherein the blood protein is serum albumin.

15. A method according to claim 13 wherein the compound is administered as a bolus.

16. A method according to claim 13 wherein the compound is administered continuosly.

* * * * *